US00PP11153P

United States Patent [19]

Zary

[11] Patent Number: Plant 11,153

[45] Date of Patent: Dec. 14, 1999

[54] FLORIBUNDA ROSE PLANT NAMED 'JACSUNOV'

[75] Inventor: Keith W. Zary, Thousand Oaks, Calif.

[73] Assignee: Bear Creek Gardens, Inc., Medford, Oreg.

[21] Appl. No.: 09/066,286

[22] Filed: Apr. 24, 1998

[51] Int. Cl.[6] ..... A01H 5/00

[52] U.S. Cl. ..... Plt./149

[58] Field of Search ..... Plt./149, 150, 151, Plt./141

*Primary Examiner*—Howard J. Locker

*Attorney, Agent, or Firm*—Klarquist Sparkman Campbell Leigh & Whinston

[57] ABSTRACT

Floribunda rose plant having good clustering ability and good production of cut flowers of a bright dark pink color and fairly large size on long stems.

1 Drawing Sheet

The present invention relates to a new and distinct variety of rose plant of the floribunda class, which was originated by me by crossing the variety 'INTERlien', (U.S. Plant Pat. No. 7,368), with an unnamed seedling.

The primary objective of this breeding was to produce a new rose variety having the clustering ability, strong foliage and good cut flower production of the female parent, combined with the larger flower size of the male parent. The objective was substantially achieved, along with other desirable improvements, as evidenced by the following unique combination of characteristics that are outstanding in the new variety and that distinguish it from its parents, as well as from all other varieties of which I am aware:

1. Good clustering ability;
2. Fairly large flower size;
3. Bright dark pink flowers;
4. Long stems; and
5. Good production of cut flowers.

'JACsunov' is a clustering floribunda developed as a cut flower rose whose flowers can be sold in clusters. Production is 140–150 stems/$m^2$ of greenhouse.

Asexual reproduction of this new variety by budding, as performed at Wasco, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'INTERlien', U.S. Plant Pat. No. 7,368.

*Pollen parent.*—Unnamed seedling (KORenlo× JACreb).

Classification:

*Botanical.*—Rosa hybrida.

*Commercial.*—Floribunda.

FLOWER

Observations made from specimens grown in a greenhouse environment at Somis, Calif., from January 1997 to February 1998.

Blooming habit: Continuous.

Bud:

*Size.*—About one inch long when the petals start to unfurl.

*Form.*—Long, pointed ovoid.

*Color.*—When sepals first divide, bud color is Red-Purple Group 58C. When half blown, the upper sides of the petals are Red-Purple Group 58B, and the lower sides of the petals are Red-Purple Group 58C.

*Sepals.*—Color: Green Group 137C. Surface texture: Covered in fine hairs. There are three lightly appendaged sepals. There are two unappendaged sepals with hairy edges.

*Receptacles.*—Color; Green Group 137D. Shape: Funnel. Size: Large (about ⅜"×⅜"). Surface: Smooth.

*Peduncle.*—Length: Short (about 2"). Surface: Smooth. Color: Green Group 137D. Strength: Stiff, erect.

Bloom:

*Size.*—Medium. Average open diameter is about 3 to 3½ inches.

*Borne.*—In flat clusters of five to seven flowers.

*Stems.*—Long (average about 20–24"), strong.

*Form.*—When first open: High centered. Permanence: Retains its form to the end.

*Petalage.*—Number of petals under normal conditions: 30–35.

*Color.*—The upper sides of the petals are Red-Purple Group 58B. The reverse sides of the petals are Red-Purple Group 58C. The base of each petal has a small (3/16"×3/16"), White Group 155B half moon at the point of attachment. The major color on the upper sides is Red-Purple Group 58B.

*Variegations.*—Greenish white streaks on the guard petals.

*Discoloration.*—At the end of the first day: No change. At the end of the third day: No change. No change in color to petal drop.

*Fragrance.*—Slight.

Petals:

*Texture.*—Thick.

*Shape.*—Round.

*Form.*—Edges slightly quilled.

*Arrangement.*—Imbricated. Petaloids in the center: Few, small.

*Persistence.*—Petals drop off cleanly before drying.

*Lastingness.*—On the plant: Fair (6–7 days). As a cut flower: Long (10 days ).

Reproductive parts:

*Anthers.*—Size: Medium. Quantity: Many. Color: Yellow. Arrangement: Regular around styles.

*Filaments.*—Color: Greenish white.
*Pollen.*—Color: Gold yellow.
*Styles.*—Color: Reddish.
*Stigmas.*—Color: Greenish white.

Plant:
*Form.*—Bush.
*Growth.*—Vigorous; upright; branching. At maturity, in the greenhouse after one year, height is 5½ feet, width is 4 feet.

Foliage: Number of leaflets on normal mid-stem leaves: Five or seven.
*Size.*—Large (7" long×5½" wide).
*Quantity.*—Abundant.
*Color.*—New foliage: Upper and lower side: Greyed-Purple Group 183C. Old foliage: Upper side: Green Group 139A. Lower side: Green Group 139C.

Leaflets:
*Shape.*—Pointed oval.
*Texture.*—Leathery, glossy.
*Edge.*—Serrated.
*Serration.*—Single, small.
*Petiole rachis.*—Color: Green Group 139A.
*Petiole underside.*—Rough with prickles.
*Stipules.*—Long (1"), with a very fine serration.
*Disease resistance.*—Resistant to mildew under normal growing conditions at Somis, Calif.

Wood:
*New wood.*—Color: Greyed-Purple Group 183C. Bark: Smooth.
*Old wood.*—Color: Green Group 137A. Bark: Smooth.

Prickles:
*Quantity.*—On main canes from base: Ordinary. On laterals from main canes: Ordinary.
*Form.*—Long, hooked slightly downward.
*Color when young.*—Red-Purple Group 59B.

Small prickles:
*Quantity.*—On main stalks: None. On laterals: None.

I claim:

1. A new and distinct variety of rose plant of the floribunda class, as herein shown and described, characterized particularly by its good clustering ability and good production of cut flowers of a bright dark pink color and fairly large size on long stems.

* * * * *

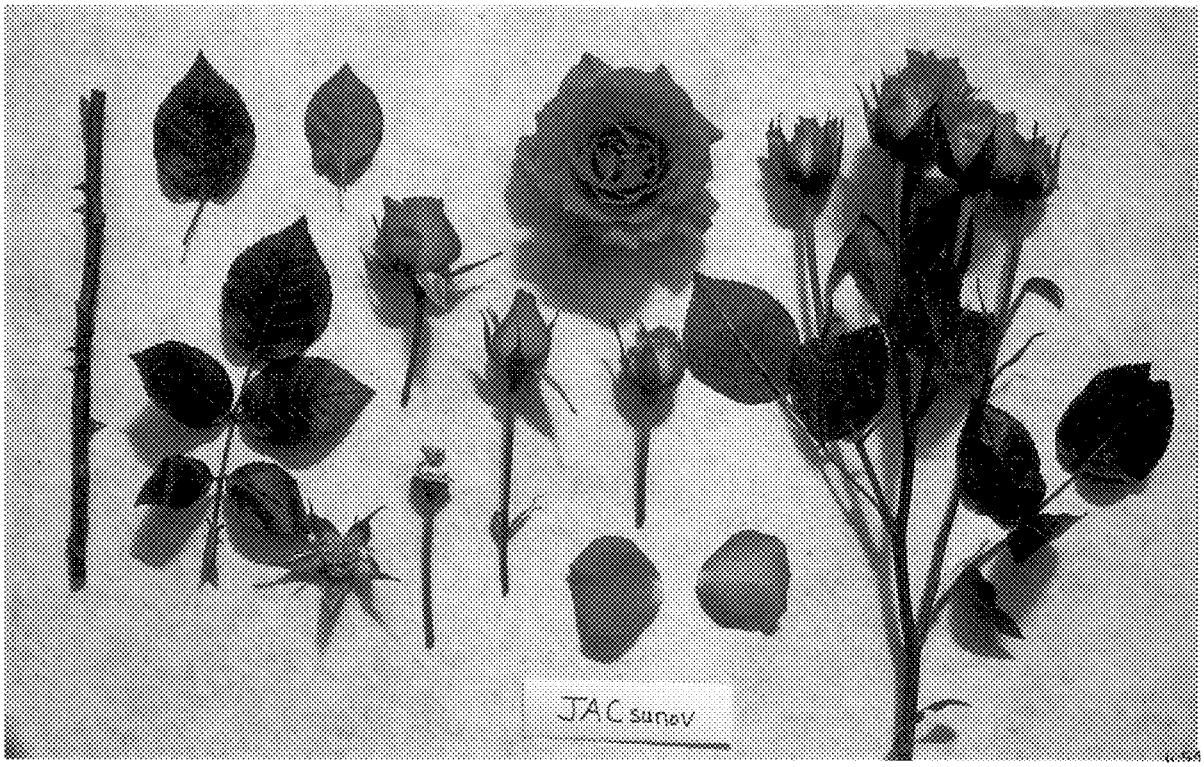
JAC sunev